United States Patent [19]
Portmann

[11] Patent Number: 6,156,907
[45] Date of Patent: Dec. 5, 2000

[54] PROCESS FOR PREPARING 1-SUBSTITUTED 4-CYANO-1,2,3-TRIAZOLES

[75] Inventor: Robert Portmann, Pratteln, Switzerland

[73] Assignee: Novartis AG, Basel, Switzerland

[21] Appl. No.: 09/214,698

[22] PCT Filed: Jul. 10, 1997

[86] PCT No.: PCT/EP97/03671

§ 371 Date: Jan. 8, 1999

§ 102(e) Date: Jan. 8, 1999

[87] PCT Pub. No.: WO98/02423

PCT Pub. Date: Jan. 22, 1998

[30] Foreign Application Priority Data

Jul. 11, 1996 [CH] Switzerland .............. 1747/96

[51] Int. Cl.$^7$ ............... C07D 249/04; C07D 249/06; C07D 403/04; C07D 407/04; C07D 409/04
[52] U.S. Cl. ............... 548/255; 540/485; 546/268.4; 548/250; 548/251; 548/254
[58] Field of Search ............................... 548/255

[56] References Cited

U.S. PATENT DOCUMENTS 4,789,680 12/1988 Meier .

FOREIGN PATENT DOCUMENTS 199 262 10/1986 European Pat. Off. .

OTHER PUBLICATIONS

Database WPI Abstract XP002043428 (1981).
WPIDS Abstract 84–190298 (1984).
A. Derdour et al., Bull. De La Societe Chim. De France, pp. 69–78 (1990) *.
R.G.Micetich, Canadian Jour. of Chem., vol. 47, pp. 3753–3755 (1970) *.

*Primary Examiner*—Patricia L. Morris
*Attorney, Agent, or Firm*—Joseph J. Borovian

[57] ABSTRACT

The invention relates on the one hand to a novel preparation of compounds of the formula (I)

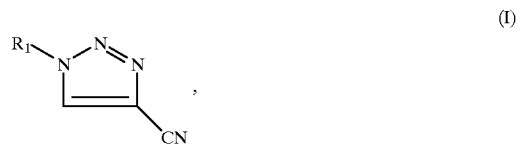

in which $R_1$ is an aromatic or heteroaromatic radical, aromatic-aliphatic or heteroaromatic-aliphatic radical, a heterocyclic radical, a cycloaliphatic radical, a cycloaliphatic-aliphatic radical or an aliphatic radical,
and on the other hand to novel compounds of the formula (I).

6 Claims, No Drawings

PROCESS FOR PREPARING 1-SUBSTITUTED 4-CYANO-1,2,3-TRIAZOLES

BACKGROUND OF THE INVENTION

1-Substituted 1H-1,2,3-triazoles are widely used industrially. For example, the European Patent Applications with the publication nos. 114347 A2 (EP 114347) and 199262 A1 (EP 199262) describe appropriate triazoles having anticonvulsive action. Compounds of this type are prepared, for example, by reaction of an arylalkyl azide with an alkyne derivative followed, if desired, by subsequent chemical conversions. Actual embodiments can be seen, for example, from the working examples of EP 199262 and EP 114347.

It is the aim of a variety of efforts to develop for pharmaceutical active ingredients production processes which are easy to manipulate and economical, result in high yields and ecologically have as few objections as possible.

The invention relates to a novel process for the preparation of 1-substituted 1H-1,2,3-triazole-4-carbonitriles, to novel intermediates and to their use for the production, for example, of pharmaceutical active ingredients.

DESCRIPTION OF THE INVENTION

The invention relates on the one hand to a novel preparation of compounds of the formula (I)

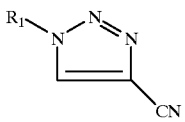

in which $R_1$ is an aromatic or heteroaromatic radical, aromatic-aliphatic or heteroaromatic-aliphatic radical, a heterocyclic radical, a cycloaliphatic radical, a cycloaliphatic-aliphatic radical or an aliphatic radical, and on the other hand to novel compounds of the formula (I).

An aromatic radical is, for example, mono- or bicyclic carbocyclic aryl which is unsubstituted or mono- or polysubstituted, such as di- or trisubstituted, for example phenyl, naphthyl or biphenylyl.

A heteroaromatic radical is, for example, mono- bi- or tricyclic heteroaryl, for example a 5- or 6-membered and monocyclic radical, which contains up to and including four identical or different heteroatoms, such as oxygen, sulfur or nitrogen, preferably 1, 2, 3 or 4 nitrogen atoms, an oxygen or a sulfur atom.

Suitable 5-membered heteroaryl radicals are, for example, monoaza-, diaza-, triaza-, tetraaza-, monooxa- or monothiacyclic heteroaryl radicals, such as pyrrolyl, pyrazolyl, imidazolyl, triazolyl, tetrazolyl, furyl and thienyl, while possible 6-membered radicals are, in particular, pyridyl radicals.

In an aromatic-aliphatic radical, the aromatic moiety, for example, has the meaning which is indicated above for aromatic radicals, while an aliphatic radical is, for example, lower alkyl, lower alkenyl or lower alkynyl. An aromatic-aliphatic radical is, for example, phenyl-lower alkyl, phenyl-lower alkenyl or phenyl-lower alkynyl, furthermore naphthyl-lower alkyl.

In a heteroaromatic-aliphatic radical, the heteroaromatic moiety, for example, h as the meaning which is indicated above for heteroaromatic radicals, while an aliphatic radical is, for example, lower alkyl, lower alkenyl or lower alkynyl. A heteroaromatic-aliphatic radical is, for example, pyridyl-lower alkyl.

A heterocyclic radical is, for example, a 5- or 6-membered monocyclic or a bi- or tricyclic radical which contains up to and including four identical or different heteroatoms, such as nitrogen, oxygen or sulfur, preferably one, two or three nitrogen atoms, a sulfur and an oxygen atom. It is also possible for one or two benzene rings to be fused to an appropriate heterocyclic radical. A heterocyclic radical of this type, for example, is a partially hydrogenated 2-oxobenzazepine, such as 2,3,4,5-tetrahydro-2-oxo-1H-1-benzazepine.

A cycloaliphatic radical is, for example, cycloalkyl or furthermore cycloalkenyl, which in each case are unsubstituted or mono- or polysubstituted, e.g. disubstituted, e.g. by lower alkyl, carboxyl or lower alkoxycarbonyl.

A cycloaliphatic-aliphatic radical is, for example, cycloalkyl-lower alkyl or furthermore cycloalkenyl-lower alkyl.

An aliphatic radical is, for example, lower alkyl, lower alkenyl or furthermore lower alkynyl, which are unsubstituted or in each case mono-or polysubstituted, e.g. disubstituted, e.g. by halogen, by free or esterified or amidated carboxyl, such as lower alkoxycarbonyl, carbamoyl or mono- or di-lower alkylated carbamoyl, by hydroxyl which can also be etherified, by $S(O)_m$—$R^0$ or by a hydrocarbon radical, such as lower alkyl, lower alkenyl or lower alkynyl, which in turn can be unsubstituted or substituted, for example by halogen or hydroxyl; m being 0, 1 or 2 and $R^0$ being an aliphatic radical. Etherified hydroxyl is, in particular, lower alkoxy or lower alkenyloxy, furthermore phenyl-lower alkoxy and phenoxy.

Aromatic and heteroaromatic radicals can be unsubstituted or mono- or polysubstituted, e.g. di- or trisubstituted, for example by substituents selected from: halogen, hydroxyl which can also be etherified, $S(O)_m$—$R^0$ and a hydrocarbon radical which in turn can be unsubstituted or substituted, for example by halogen or hydroxyl; m being 0, 1 or 2 and $R^0$ being an aliphatic radical.

If not defined differently, the general definitions used above and below have the following meanings:

The expression "lower" means that appropriate groups and compounds in each case in particular contain up to and including 7, preferably up to and including 4, carbon atoms.

Naphthyl is 1- or 2-naphthyl.

Biphenylyl is 2-, 3- or, in particular, 4-biphenylyl.

Pyrrolyl is, for example, 2- or 3-pyrrolyl. Pyrazolyl is 3- or 4-pyrazolyl. Imidazolyl is 2- or 4-imidazolyl. Triazolyl is, for example, 1H-1,2,4-triazol-2-yl or 1,3,4-triazol-2-yl. Tetrazolyl is, for example, 1,2,3,4-tetrazol-5-yl, furyl is 2- or 3-furyl and thienyi is 2- or 3-thienyl, while pyridyl can be 2-, 3- and 4-pyridyl.

Lower alkyl is in particular $C_1$–$C_7$alkyl, e.g. methyl, ethyl, n-propyl, isopropyl, n-butyl, isobutyl, sec-butyl, tert-butyl, and furthermore includes corresponding pentyl, hexyl and heptyl radicals. $C_1$–$C_4$alkyl is preferred.

Lower alkenyl is in particular $C_3$–$C_7$alkenyl and is for example, 2-propenyl or 1-, 2- or 3-butenyl. $C_3$–$C_5$alkenyl is preferred.

Lower alkynyl is in particular $C_3$–$C_7$alkynyl and is preferably propargyl.

Phenyl lower alkyl is in particular phenyl-$C_1$–$C_4$alkyl and is preferably benzyl, 1- and 2-phenethyl, while phenyl-lower alkenyl and phenyl-lower alkynyl are in particular phenyl-$C_3$–$C_5$alkenyl and -alkynyl, in particular 3-phenylallyl and 3-phenylpropargyl.

Naphthyl-lower alkyl is in particular naphthyl-$C_1$–$C_4$alkyl and is, for example, 1- or 2-naphthylmethyl, -ethyl, -n-propyl or -n-butyl.

Pyridyl-lower alkyl is in particular pyridyl-$C_1$–$C_4$alkyl and is, for example, 2-, 3- or 4-pyridylmethyl, -ethyl, -n-propyl or -n-butyl.

Cycloalkyl is, for example, $C_3$–$C_8$acycloalkyl, which can be unsubstituted or substituted, for example by lower alkyl and is, for example, cyclopropyl, cyclobutyl, cyclopentyl, cyclohexyl and cycloheptyl. Cyclopentyl and cyclohexyl are preferred.

Cycloalkenyl is in particular $C_3$–$C_7$cycloalkenyl and is preferably cyclopent-2-enyl, cyclopent-3-enyl, cyclohex-2-enyl and cyclohex-3-enyl.

Cycloalkyl-lower alkyl is in particular $C_3$–$C_8$cycloalkyl-$C_1$–$C_4$alkyl and is, for example, cyclopentyl- or cyclohexylmethyl or -ethyl, while cycloalkyl-lower alkenyl is in particular $C_3$–$C_8$cycloalkyl-$C_3$–$C_4$alkenyl and is, for example, cyclopentyl- or cyclohexylprop-2-enyl or cyclo-2-butenyl.

Lower alkoxy is in particular $C_1$–$C_7$alkoxy and is, for example, methoxy, ethoxy, n-propyloxy, isopropyloxy, n-butyloxy, isobutyloxy, sec-butyloxy, tert-butyloxy and furthermore includes corresponding pentyloxy, hexyloxy and heptyloxy radicals. $C_1$–$C_4$alkoxy is preferred.

Lower alkenyloxy is in particular $C_3$–$C_7$alkenyloxy and is, for example, allyloxy or but-2-enyloxy or but-3-enyloxy. $C_3$–$C_5$alkenyloxy is preferred.

Phenyl-lower alkoxy is in particular phenyl-$C_1$–$C_4$alkoxy, such as benzyloxy, 1- or 2-phenylethoxy, 3-phenylpropyloxy or 4-phenylbutyloxy.

Lower alkoxycarbonyl is in particular $C_2$–$C_8$alkoxycarbonyl and is, for example, methoxy-, ethoxy-, propyloxy- or pivaloyloxycarbonyl. $C_2$–$C_5$alkoxycarbonyl is preferred.

Halogen is in particular fluorine, chlorine or bromine, and furthermore includes iodine.

Japanese Patent Application J 56 127-363 describes a synthesis possibility for 1-substituted 1H-1,2,3-triazole-4-carbonitrile. Accordingly, the preparation of triazoles of this type takes place according to the following two-stage reaction scheme:

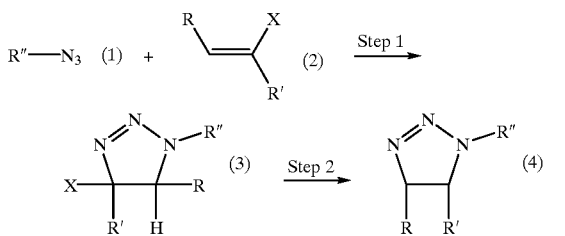

In this case, R', inter alia, can also be cyano and X can be halogen, such as chlorine or bromine. However, only reactions with bromine derivatives of the formula (2) are exemplified. Actual reactions which lead to compounds (3) and (4) in which R' is cyano are described just as little in the working examples.

The procedure described in J 56 127-363 has the following disadvantages: On the one hand it is clearly a process to be carried out in two separate steps, in which the formation of the corresponding dihydrotriazoles (3) is extremely time-consuming, also these intermediates must be isolated first before they can react further in the second step. Thus appropriate reactions are described whose first stage is complete only after 4 days to 3 weeks, before the next step can take place. This procedure is too troublesome and complicated for a production process.

In contrast, the process according to the invention proves clearly superior. Thus the formation of compounds of the formula (I) is carried out in one step and in one reaction vessel without it being necessary to isolate intermediates. Furthermore, when using the reaction according to the invention high yields are already attained after approximately 24 hours.

The process according to the invention is characterized by the following reaction equation:

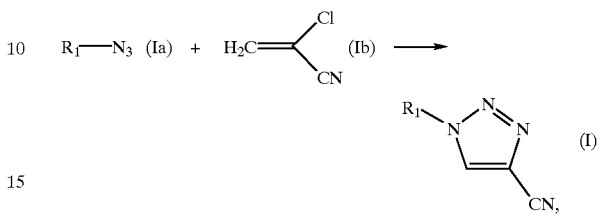

the variable $R_1$ being defined as indicated above.

The invention relates in particular to the preparation of compounds of the formula (I) in which $R_1$ is phenyl, naphthyl, biphenylyl, pyrrolyl, pyrazolyl, imidazolyl, triazolyl, tetrazolyl, furyl, thienyl, pyridyl, phenyl-lower alkyl, phenyl-lower alkenyl, phenyl-lower alkynyl, naphthyl-lower alkyl, pyridyl-lower alkyl, a partially hydrogenated 2-oxobenzazepine, cycloalkyl, cycloalkenyl, cycloalkyl-lower alkyl or cycloalkenyl-lower alkyl, and also lower alkyl, lower alkenyl or lower alkynyl which are unsubstituted or in each case mono- or polysubstituted by substituents selected from halogen, carboxyl, lower alkoxycarbonyl, carbamoyl, mono- or di-lower alkylated carbamoyl, hydroxyl, lower alkoxy, lower alkenyloxy, phenyl-lower alkoxy and phenoxy; it being possible for aromatic and heteroaromatic radicals to be unsubstituted or mono- or polysubstituted by substituents selected from: halogen, lower alkoxy, lower alkenyloxy, phenyl-lower alkoxy, phenoxy, $S(O)_m$—$R^0$, m being 0, 1 or 2 and $R^0$ being lower alkyl, lower alkenyl and lower alkynyl, which are unsubstituted or in each case mono- or polysubstituted by substituents selected from halogen, hydroxyl, lower alkoxy, lower alkenyloxy, phenyl-lower alkoxy, phenoxy, carboxyl and lower alkoxycarbonyl.

The invention relates in particular to the preparation of compounds of the formula (I) in which $R_1$ is phenyl-lower alkyl, phenyl-lower alkenyl, phenyl-lower alkynyl, naphthyl-lower alkyl, pyridyl-lower alkyl, a partially hydrogenated 2-oxobenzazepine, cycloalkyl-lower alkyl, cycloalkenyl-lower alkyl or lower alkyl which is substituted by carboxyl or lower alkoxycarbonyl; it being possible for aromatic and heteroaromatic radicals to be unsubstituted or mono- or polysubstituted by substituents selected from: halogen, lower alkyl, lower alkenyl, lower alkynyl, lower alkoxy, lower alkenyloxy, phenyl-lower alkoxy, phenoxy and $S(O)_m$—$R^0$, $R^0$ being lower alkyl, lower alkenyl or lower alkynyl, and m being 0, 1 or 2.

The invention relates in particular to the preparation of compounds of formula (I) in which $R_1$ is 2,3,4,5-tetrahydro-1H-2-oxobenzazepin-1-yl or lower alkyl which is substituted by lower alkoxycarbonyl.

The invention relates in particular to the preparation of compounds of the formula (I) in which $R_1$ is phenyl-$C_1$–$C_4$alkyl substituted by lower alkyl, halogen and/or trifluoromethyl.

The invention relates in particular to the preparation of compounds of the formula (I) in which $R_1$ is benzyl substituted by lower alkyl, halogen and/or trifluoromethyl.

The invention relates in particular to the preparation of compounds of the formula (I) in which $R_1$ is 2-fluorobenzyl, 2-chloro-6-fluorobenzyl or 2,6-difluorobenzyl.

The invention relates primarily to the preparation of 4-cyano-1-(2,6-difluorobenzyl)-1H-1,2,3-triazole.

The invention relates in particular to the preparation of the N-substituted 4-cyano-1H-1,2,3-triazole compounds mentioned in the working examples.

The reaction according to the invention of the azide (Ia) with 2-chloroacrylonitrile (Ib) to give a compound of the formula (I) comprises working in a two-phase system. The two-phase system consists of an organic and an aqueous phase. The organic phase consists essentially of the starting materials of the formulae (Ia) and (Ib), if desired in the presence of an organic solvent or diluent. The hydrogen chloride formed in the reaction is poorly soluble in this phase.

Appropriate organic solvents or diluents are, for example: aprotic solvents, for example weakly basic amides, such as dimethylformamide, or aliphatic, araliphatic and aromatic hydrocarbons or ethers, for example $C_6$–$C_{10}$ alkanes or lower-alkylated benzene, such as xylene or toluene, or di-lower alkyl ethers, such as dibutyl ether, anisole, or cyclic ethers, such as dioxane.

The hydrogen chloride should be readily soluble, but the starting materials poorly soluble, in the aqueous phase. Advantageously the aqueous phase consists of water.

Primarily, the two-phase system is formed from the organic phase, consisting of the starting materials (Ia) and (Ib), and from water.

The results shown in Table 2 of the working examples illustrate that the best yields are attained in the two-phase system consisting on the one hand of the starting materials and on the other hand of water.

2-Chloroacrylonitrile can polymerize both under acidic and basic conditions. On reaction of an azide of the formula (Ia) with 2-chloroacrylonitrile, hydrogen chloride is released, i.e. a strongly acidic medium results, which favors such a polymerization. This is also the case when an organic solvent is added, i.e. only one liquid phase is present. Additionally, the reaction is slowed down by dilution, the more organic solvent used. These disadvantages can be avoided if a two-phase system is used instead of a single-phase organic system. The azide of the formula (Ia) forms with 2-chloroacrylonitrile one, concentrated phase, while primarily water is the second phase. During the reaction resulting hydrogen chloride is continuously extracted into the aqueous phase and thus reduces the danger of the polymerization of 2-chloroacrylonitrile. Moreover, the greatest possible reaction rate is attained in the two-phase system.

The amount of water should at least be proportioned so that the hydrogen chloride released in the reaction is soluble in the aqueous phase.

Per mole of compound of formula (Ia), preferably approximately 1 to approximately 2 mol, primarily approximately 1.5 mol, of 2-chloroacrylonitrile (Ib) are employed. As the results presented in Table 1 of the working examples show, approximately 1.5 mol equivalents of 2-chloroacrylonitrile are sufficient for an optimum yield. Thus in the preparation of 4-cyano-2,6-difluorobenzyl-1H-1,2,3-triazole with a reaction time of approximately 24 hours a desirable yield of over 90% of theory is attained.

The reaction according to the invention is carried out, for example, in a temperature range from approximately 20° C. to approximately 85° C., in particular from approximately 60° C. to approximately 85° C., primarily from approximately 75° C. to approximately 85° C.

The invention furthermore relates to novel compounds of the formula (I).

The invention primarily relates to the compound 4-cyano-1-(2,6-difluorobenzyl)-1H-1,2,3-triazole.

The invention furthermore relates to the use of a compound of the formula (I) for the production of a pharmaceutical active ingredient, for example of the resulting products according to EP 114347 and EP 199262. Especially the resulting compounds of the claims of both published patent applications are herewith incorporated by reference into the instant specification. The corresponding preparation of compounds of this type starting from compounds of the formula (I) is carried out, for example, in a manner known per se. For example, the nitrites of the formula (I) can thus be converted by hydrolysis into the corresponding carboxamides and these can be converted by further hydrolysis into the corresponding carboxylic acids.

The invention relates primarily to the use of the compound 4-cyano-1-(2,6-difluorobenzyl)-1H-1,2,3-triazole for the production of a pharmaceutical active ingredient, especially for the manufacture of 1-(2,6-difluorobenzyl)-1H-1,2,3-triazol-4-carboxamide or of a pharmaceutically acceptable salt thereof.

The following examples serve to illustrate the present invention, but are not intended to restrict this in any case.

EXAMPLE 1

4-Cyano-1-(2,6-difluorobenzyl)-1H-1,2,3-triazole

A mixture of 2,6-difluorobenzyl azide (34.2 g), 2-chloroacrylonitrile (17.73 g) and water (125 ml) is stirred at about 80° C. for 24 hours. Excess 2-chloroacrylonitrile is distilled off by raising the external temperature to about 130° C. The semi-solid mixture is cooled to about 40° C. and the suspension is treated with cyclohexane (50 ml), brought to about 20° C. and stirred for about 2 hours. The product is isolated by filtration, washed with cyclohexane (75 ml) and then with water (50 ml). The moist product is mixed with water (100 ml), the suspension is filtered and the product is washed with water (50 ml) and dried in vacuo at about 60° C. Yield: 38.04 g=86%.

EXAMPLE 2

4-Cyano-1-(2,6-difluorobenzyl)-1H-1,2,3-triazole

A mixture of 2,6-difluorobenzyl azide (34.2 g), 2-chloroacrylonitrile (17.73 g) and water (125 ml) is stirred at about 80° C. for 48 hours. Excess 2-chloroacrylonitrile is distilled off by raising the external temperature to about 130° C. The semi-solid mixture is cooled to about 40° C. and the suspension is treated with cyclohexane (50 ml), brought to about 20° C. and stirred for about 2 hours. The product is isolated by filtration, washed with cyclohexane (75 ml) and then with water and dried in vacuo at about 60° C. Yield: 40.91 g=93%.

EXAMPLE 3

4-Cyano-1-(2,6-difluorobenzyl)-1H-1,2,3-triazole

A mixture of 2,6-difluorobenzyl azide (34.2 g), 2-chloroacrylonitrile (26.6 g) and water (125 ml) is stirred at about 70° C. for 24 hours. Excess 2-chloroacrylonitrile is distilled off by raising the external temperature to about 130° C. The mixture is cooled to about 95° C. and the product is crystallized by seeding. After cooling to about 40° C., the suspension is treated with cyclohexane (50 ml) and brought to about 20° C., and the product is isolated by filtration, washed with cyclohexane (75 ml) and then with water and dried in vacuo at about 60° C. Yield: 36.38 g=82.6%.

EXAMPLE 4

4-Cyano-1-(2,6-difluorobenzyl)-1H-1,2,3-triazole

A mixture of 2,6-difluorobenzyl azide (34.2 g), 2-chloroacrylonitrile (26.6 g) and water (125 ml) is stirred at about 80° C. for 24 hours. Excess 2-chloroacrylonitrile is distilled off by raising the external temperature to about 130° C. The mixture is cooled to about 95° C. and the product is crystallized by seeding. After cooling to about 40° C., the suspension is treated with cyclohexane (50 ml) and brought to about 20° C., and stirred for about 2 hours. The product is isolated by filtration, washed with cyclohexane (75 ml) and then with water and dried in vacuo at about 60° C. Yield: 43.13 g=98%.

EXAMPLE 5

4-Cyano-1-(2,6-difluorobenzyl)-1H-1,2,3-triazole

A mixture of 2,6-difluorobenzyl azide (6.75 g), 2-chloroacrylonitrile (7.0 g) and water (20 ml) is stirred at about 80° C. for 12 hours. Excess 2-chloroacrylonitrile is distilled off by raising the external temperature to about 120° C. The mixture is cooled to about 20° C. and the crystallized product is isolated by filtration and washed with water. The moist product is dried in vacuo at about 60° C. Yield: 8.17 g=93%. For purification, the product (8.17 g) is dissolved in toluene (40 ml) at 80° C. and treated with bleaching earth (0.24 g), and the mixture is filtered hot. The filtrate is concentrated to about 20 ml and the resulting crystal magma is stirred at 0° C. for 1 hour. After filtering, washing with toluene and drying, a white product (7.72 g) of m.p. 115.5–116.5° C. is obtained.

EXAMPLE 6

4-Cyano-(2,6-difluorobenzyl)-1H-1,2,3-triazole

A mixture of 2,6-difluorobenzyl azide (34.2 g), 2-chloroacrylonitrile (35.46 g) and water (125 ml) is stirred at about 80° C. for 24 hours. Excess 2-chloroacrylonitrile is distilled off by raising the external temperature to about 130° C. The mixture is cooled to about 40° C. and the suspension is treated with cyclohexane (50 ml), brought to about 20° C., and stirred for about 2 hours. The product is isolated by filtration, washed with cyclohexane (75 ml) and then with water (50 ml). The moist product is mixed with water (100 ml), the suspension is filtered and the product is washed with water (50 ml) and dried in vacuo at about 60° C. Yield: 42.87 g=97%.

TABLE 1

| Example | Mol equivalent of 2-chloroacrylonitrile | Temperature | Reaction time | Yield |
|---------|-----------------------------------------|-------------|---------------|-------|
| 1 | 1.0 | 80° C. | 24 h | 86% |
| 2 | 1.0 | 80° C. | 48 h | 93% |
| 3 | 1.5 | 70° C. | 24 h | 83% |
| 4 | 1.5 | 80° C. | 24 h | 98% |
| 5 | 2.0 | 80° C. | 12 h | 93% |
| 6 | 2.0 | 80° C. | 24 h | 97% |

EXAMPLE 7

4-Cyano-(2,6-difluorobenzyl)-1H-1,2,3-triazole

A mixture of 2,6-difluorobenzyl azide (34.2 g) and 2-chloroacrylonitrile (26.6 g) is stirred at about 80° C. for 24 hours. n-Heptane (125 ml) is allowed to run in, and unreacted 2-chloroacrylonitrile and 2,6-difluorobenzyl azide as well as n-hepiarie are distilled off (distillate 50 ml) by raising the external temperature to about 130° C. The mixture is cooled to about 20° C. and the suspension is stirred at about 20° C. for 1 hour. The product is isolated by filtration and washed with n-heptane (100 ml). The product is dried in vacuo at about 60° C. Yield: 31.55 g=71.6% (beige powder).

EXAMPLE 8

4-Cyano-(2,6-difluorobenzyl)-1H-1,2,3-triazole

A mixture of 2,6-difluorobenzyl azide (34.2 g), 2-chloroacrylonitrile (26.6 g) and n-heptane (125 ml) is stirred at about 80° C. for 24 hours, whereby a suspension results. Unreacted 2-chloroacrylonitrile and 2,6-difluorobenzyl azide as well as n-heptane are distilled off (distillate 25 ml) by raising the external temperature to about 130° C. The mixture is cooled to about 20° C. and the suspension is stirred at about 20° C. for about 2 hours. The product is isolated by filtration, washed with n-heptane (100 ml) and dried in vacuo at about 60° C. Yield: 20.45 g=46.4% (beige powder).

EXAMPLE 9

4-Cyano-(2,6-difluorobenzyl)-1H-1,2,3-triazole

A mixture of 2,6-difluorobenzyl azide (34.2 g), 2-chloroacrylonitrile (26.6 g) and toluene (125 ml) is stirred at about 80° C. for 24 hours. Unreacted 2-chloroacrylonitrile and 2,6-difluorobenzyl azide as well as toluene are distilled off (distillate 100 ml) by raising the external temperature to about 130° C. After cooling to 80° C., n-heptane (100 ml) is allowed to run in. The mixture is cooled to about 20° C. and the suspension is stirred at about 20° C. for 1 hour. The product is isolated by filtration and washed with n-heptane (100 ml). The product is dried in vacuo at about 60° C. Yield: 22.31 g=50.7% (beige powder).

EXAMPLE 10

4-Cyano-(2,6-difluorobenzyl)-1H-1,2,3-triazole

A mixture of 2,6-difluorobenzyl azide (34.2 g), 2-chloroacrylonitrile (26.6 g) and absolute ethanol (125 ml) is stirred at about 77° C. for 24 hours. Unreacted 2-chloroacrylonitrile and 2,6-difluorobenzyl azide as well as ethanol are distilled off (distillate 100 ml) by raising the external temperature to about 130° C. After cooling to 70° C., water (100 ml) is allowed to run in dropwise at 70–60° C. The mixture is seeded, cooled to about 20° C. and the suspension is stirred at about 20° C. for about 1 hour. The product is isolated by filtration and washed with cyclohexane (100 ml) and then with water (100 ml). The product is dried in vacuo at about 60° C. Yield: 17.73 g=40.3% (pale beige powder).

EXAMPLE 11

4-Cyano-(2,6-difluorobenzyl)-1H-1,2,3-triazole

A mixture of 2,6-difluorobenzyl azide (34.2 g), 2-chloroacrylonitrile (26.6 g) and N,N-dimethylformamide (125 ml) is stirred at about 80° C. for 24 hours. Unreacted 2-chloro-acrylonitrile and 2,6-difluorobenzyl azide as well as N,N-dimethylformamide are distilled off (distillate 100 ml) by raising the external temperature to about 130° C. and gradually evacuating to about 100 mbar. After cooling to 100° C., water (100 ml) is allowed to run in. The crystallization of the product is initiated by seeding the brown emulsion. The mixture is cooled to about 20° C. and the suspension is stirred at about 20° C. for 30 minutes. The product is isolated by filtration and washed with water (100 ml). The product is dried in vacuo at about 60° C. Yield: 34.40 g=78.1% (beige crystals).

TABLE 2

| Example | Solvent | Mol equivalent of 2-chloro-acrylonitrile | Temperature | Reaction time | Yield |
|---|---|---|---|---|---|
| 4 | water*) | 1.5 | 80° C. | 24 h | 98% |
| 7 | without | 1.5 | 80° C. | 24 h | 72% |
| 8 | n-heptane | 1.5 | 80° C. | 24 h | 46% |
| 9 | toluene | 1.5 | 80° C. | 24 h | 51% |
| 10 | ethanol | 1.5 | 77° C. | 24 h | 40% |
| 11 | dimethylformamide | 1.5 | 80° C. | 24 h | 78% |

*) First phase = Starting materials; second phase = water

EXAMPLE 12

1-Benzyl-4-cyano-1H-1,2,3-triazole

A mixture of benzyl azide (1.33 g) and 2-chloroacrylonitrile (1.75 g) in water (5 ml) is stirred at about 80° C. for 22 hours, then excess 2-chloroacrylonitrile is distilled off in vacuo. The mixture is cooled to room temperature and the precipitated product is isolated by filtration and washed with water. After drying, the product is obtained in a yield of 1.66 g=90% of theory m.p. 78–79° C. (recrystallization from toluene/hexane).

EXAMPLE 13

4-Cyano-1-(4-cyanobenzyl)-1H-1,2,3-triazole

A mixture of 4-cyanobenzyl azide (0.8 g) and 2-chloroacrylonitrile (0.88 g) in water (5 ml) is stirred at about 80° C. for 20 hours. Excess 2-chloroacrylonitrile is distilled off in vacuo, the mixture is cooled to room temperature and the precipitated product is isolated by filtration and washed with water. The product (yield 0.92 g; 88% of theory) of m.p. 93.5–94° C. (recrystallization from ethyl acetate/toluene) is obtained after drying.

EXAMPLE 14

3-(4-Cyano-1H-1,2,3-triazol-1-yl)-2,3,4,5-tetrahydro-2-oxo-1H-1-benzazepine

A mixture of 3-azido-2,3,4,5-tetrahydro-2-oxo-1 H-1-benzazepine (1.01 g) and 2-chloro-acrylonitrile (0.95 g) in water (5 ml) is stirred at about 80° C. for 18 hours. Excess 2-chloro-acrylonitrile is distilled off in vacuo, and the precipitated product is filtered off, washed with water and dried (yield 1.1 g; 87% of theory), m.p. 214–216° C. (recrystallization from ethyl acetate/toluene).

EXAMPLE 15

Ethyl (4-cyano-1H-1,2,3-triazol-1yl)acetate

A mixture of ethyl 2-azidoacetate (1.29 g) and 2-chloroacrylonitrile (1.75 g) in water (10 ml) is stirred at about 80° C. for 16 hours. After cooling, the product is extracted with dichloromethane and the concentrated extract is purified by means of column chromatography on silica gel 60 (6 g; eluent: toluene/ethyl acetate=4:1). The purified product (yield 1.21 g; 67% of theory) of m.p. 47–48° C. (recrystallization from toluene/hexane) is obtained after concentrating the eluate and drying.

EXAMPLE 16

Ethyl 2-(4-cyano-1H-1,2,3-triazol-1-yl)-4-phenyl-(2S)-butyrate

A mixture of ethyl 2-azido-4-phenyl-(2S)-butyrate (2.33 g) and 2-chloroacrylonitrile (1.75 g) in water (25 ml) is stirred at about 80° C. for 23 hours. After cooling, the product is extracted with toluene and purified by column chromatography (30 g of silica gel 60; eluent toluene). The purified product is obtained as a yellowish oil (yield 1.84 g; 65% of theory) and characterized by $^1$H—NMR spectrum (CDCl$_3$). δ value: 1.29 (*H; t; J=7 Hz); 2.40–2.67 (4H, m); 4.20 (2H, q, J=7 Hz); 5.39 (1H, m); 7.10 (2H, dxd, J$_1$=6.6 Hz, J$_2$=1.5 Hz); 7.24 (1H, txt, J$_1$=6.6 Hz, J$_2$≦1.5 Hz); 7.31 (2h, m); 8.21 (1H, s).

EXAMPLE 17

1-(2,6-Difluorobenzyl)-1H-1,2,3-triazol-4-carboxamide

A mixture of 2,6-difluorobenzylazide (9,22 g), 2-chloroacrylonitrile (6,68 g) and water is stirred at about 82° C. for about 24 hours. 2-chloroacrylonitrile is distilled off by reasing the external temperature to about 113° C. excess. The mixture is cooled to about 40° C. and toluene (10 ml) is added. Within about 40 minutes at about 80° C. sodium hydroxide (5,5 ml—30%) is added the amide being crystallized. By raising the external temperature to 112° C., toluene is distilled off. The suspension is cooled to 20° C. and the product is isolated by filtration, washed with water (200 ml) and dried at about 60° C. in vacuo.

What is claimed is:

1. A process for preparing a compound of formula (I)

in which R$_1$ is phenyl, naphthyl, biphenylyl, pyrrolyl, pyrazolyl, imidazolyl, triazolyl, tetrazolyl, furyl, thienyl, pyridyl, phenyl-lower alkyl, phenyl-lower alkenyl, phenyl-lower alkynyl, naphthyl-lower alkyl, pyridyl-lower alkyl, a partially hydrogenated 2-oxobenzazepine, cycloalkyl, cycloalkenyl, cycloalkyl-lower alkyl or cycloalkenyl-lower alkyl, and also lower alkyl, lower alkenyl or lower alkynyl which are unsubstituted or in each case mono- or polysubstituted by substituents selected from halogen, carboxyl, lower alkoxycarbonyl, carbamoyl, mono- or di-lower alkylated carbamoyl, hydroxyl, lower alkoxy, lower alkenyloxy, phenyl-lower alkoxy and phenoxy; it being possible for aromatic and heteroaromatic radicals to be unsubstituted or mono- or polysubstituted by substituents selected from: halogen, lower alkoxy, lower alkenyloxy, phenyl-lower alkoxy, phenoxy and S(O)$_m$—R$^0$ where m is 0, 1 or 2 and R$^0$ is lower alkyl, lower alkenyl or lower alkynyl, each of which is unsubstituted or mono- or polysubstituted by substituents selected from halogen, hydroxyl, lower alkoxy, lower alkenyloxy, phenyl-lower alkoxy, phenoxy, carboxyl and lower alkoxycarbonyl, which comprises reacting an azide compound of formula (Ia)

 (Ia)

in which $R_1$ is as defined above, with 2-chloroacrylonitrile of formula (Ib)

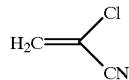 (1b)

in a two-phase system consisting of:
(1) an organic phase consisting of the staring materials of formula Ia and Ib and, optionally, an organic solvent or diluent, and
(2) an aqueous phase in which the hydrogen chloride that is released during the reaction is readily soluble, and the starting materials are poorly soluble, at a temperature range of from approximately 20° C. to approximately 85° C.

2. A process according to claim 1, wherein the two-phase system consists of (i) the starting materials and (ii) water.

3. A process according to claim 1, wherein approximately 1 to approximately 2 mol of 2-chloroacrylonitrile (Ib) is employed in the reaction per mole of compound of the formula (Ia).

4. A process according to claim 1, wherein the reaction is carried out in a temperature range from approximately 75° C. to approximately 85° C.

5. A process according to claim 1, wherein a compound of the formula (I) is prepared in which $R_1$ is 2-fluorobenzyl, 2-chloro-6-fluorobenzyl or 2,6-difluorobenzyl.

6. A process according to claim 1, wherein 4-cyano-1-(2, 6-difluorobenzyl)-1H-1,2,3-triazole is prepared.

* * * * *